United States Patent [19]

Cordon et al.

[11] 3,989,814
[45] Nov. 2, 1976

[54] CALCIUM PYROPHOSPHATE ABRASIVE SYSTEM FOR DENTIFRICE

[75] Inventors: Martin Cordon, Highland Park; James Norfleet, Plainfield, both of N.J.

[73] Assignee: Colgate-Palmolive Company, New York, N.Y.

[22] Filed: Mar. 17, 1975

[21] Appl. No.: 559,117

Related U.S. Application Data

[63] Continuation-in-part of Ser. No. 544,618, Jan. 28, 1975.

[52] U.S. Cl. .................................................. 424/57
[51] Int. Cl.² ........................................ A61K 7/16
[58] Field of Search ............................... 424/49–58

[56] References Cited

UNITED STATES PATENTS

| | | | |
|---|---|---|---|
| 3,622,662 | 11/1971 | Roberts | 424/58 |
| 3,887,701 | 6/1975 | Nachtigal | 424/52 |

*Primary Examiner*—Lewis Gotts
*Assistant Examiner*—Cary Owens
*Attorney, Agent, or Firm*—Robert L. Stone; Murray M. Grill; Herbert S. Sylvester

[57] ABSTRACT

Dentifrice possessing enhanced polishing characteristics containing abrasive system including at least calcium pyrophosphate and a non-toxic zinc compound in an amount to provide at least about 0.0065% of zinc to the dentifrice.

7 Claims, No Drawings

CALCIUM PYROPHOSPHATE ABRASIVE SYSTEM FOR DENTIFRICE

This application is a continuation-in-part of U.S. patent application Ser. No. 544,618, filed Jan. 28, 1975, and incorporates the disclosure thereof by reference.

Calcium pyrophosphate is an abrasive material which commonly can provide dentifrices in which it is incorporated with a radioactive enamel abrasion value (REA) as high as about 450 or more. Even when the REA value of a calcium pyrophosphate abrasive toothpaste is lower than 450, it would be desirable to ameliorate the enamel abrasivity. To achieve this end, this invention relates to a dentifrice having superior cleaning and polishing characteristics containing an abrasive system including at least calcium pyrophosphate, preferably present in amount of at least about 7.5% by weight of the dentifrice, more preferably about 20–75% and most preferably about 40–50%; and a non-toxic zinc compound in an amount to provide at least about 0.0065% by weight of zinc to the dentifrice, to reduce the enamel abrasivity.

Conventional dentifrices used in the daily brushing and cleaning of teeth heretofore have not provided the desired degree of polishing action. This has been largely due to the difficulty in selecting suitable abrasives which will afford maximum removal of difficult stains and debris without damaging the enamel surfaces of the teeth. It is consequently desirable to formulate a composition which not only cleans teeth but also polishes teeth to a high luster, both for aesthetic reasons as well as for oral hygiene. Highly polished surfaces appear to be less receptive to the retention of plaque and oral debris.

The polishing of teeth occurs when an abrasive planes off irregularities of the enamel tooth surfaces, the resulting smooth surfaces appearing as highly polished planes.

The function of an abrasive substance in formulations intended for use in the oral cavity is to remove various deposits, including pellicle film from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasive used in dental compositions, such as dicalcium phosphate, although not unduly abrasive to tooth tissue, are not as effective as the harder abrasives in removing these undesirable deposits from the teeth. However, hard abrasives can present serious problems when present in dental preparations since their outstanding abrasive characteristics are likely to cause undue abrasion to the oral hard tissues (enamel, dentin and cementum).

It has now been found that the addition of a non-toxic zinc compound, in an amount to provide at least about 0.0065% by weight of zinc, to a dentifrice containing calcium pyrophosphate dental abrasive material effects a substantial reduction in the enamel abrasion thereof. This permits preparation of dentifrice formulations which give superior polishing without encountering undue enamel abrasion.

Accordingly, a dentifrice possessing superior polishing action without increasing the enamel abrasivity thereof can be formulated comprising an abrasive system including at least calcium pyrophosphate and a non-toxic zinc compound in an amount to provide at least about 0.0065% by weight of zinc to the dentifrice, to reduce the enamel abrasivity.

The zinc compounds which have been found to be particularly effective in reducing the radioactive enamel abrasion of abrasive materials include zinc oxide and zinc chloride in amounts as low as 0.01% to about 1.0% by weight of the total formulation. Larger amounts may be utilized, although a maximum of 1.0% by weight is preferred. Although the zinc compounds substantially reduced enamel abrasion, they had little effect on dentin abrasion.

Calcium pyrophosphate dentifrice abrasive is discussed in "Chapter XIV. Dentifrices" of *Cosmetics, Science and Technology*, Edited by Balsam and Sagarin, Second Edition, Vol. 1 Wiley-Interscience, New York, London, Sydney and Toronto, 1972, particularly at pages 479–480 and in the references cited therein. It provides a dentifrice with substantial abrasivity to enamel. Commercially it has been used in dentifrices in amount of about 40% by weight and has been observed to have REA values of about 250–450.

In addition to calcium pyrophosphate, an additional dental abrasive may be included in the dentifrice.

The additional abrasive is typically soft in abrasiveness on enamel by comparison, and may be, for instance, any of those conventionally employed in toothpaste, such as hydrated alumina, insoluble sodium metaphosphate, dicalcium phosphate dihydrate, calcium carbonate, silica xerogels of the known density or intermediate density types (such as those sold under the name Syloid 63 or Syloid 72 or Syloid 74), alkali metal or alkaline earth metal aluminosilicates (such as those having a refractive index of about 1.44–1.47, and containing at least about 70% silica, up to about 10% alumina, up to about 20% by weight of moisture and up to about 10% by weight of sodium oxide, the moisture content preferably being about 10–20% by weight, measured by loss at 1000° C and the typical content of sodium oxide being about 5–10% by weight), kappa alumina (such as described in U.S. Pat. No. 3,003,919); synthetic resins (such as described in British Pat. No. 995,351); composite abrasive particles in which a hard mineral is coated with, or embedded in, a synthetic resin (the mineral being, for instance, crystalline silica, e.g., quartz, SiC, anhydrous alumina, hematite, zirconium silicate, etc., and the coating being, for instance, an impervious cross-linked thermoset synthetic resin such as melamine-formaldehyde resin, urea-formaldehyde, pheonol-formaldehyde, or epoxy resins or polymers or copolymers of compounds having two or more polymerizable ethylenically unsaturated groups, e.g., diallyl phthalate polymers (such as described in U.S. Pat. No. 3,151,027).

The soft dental abrasive may have a particle size about 2 to 40 microns and may also be present in the form of relatively large agglomerates (of the individual particles) of such size as to be visible to the naked eye but easily reduced to the fine impalpable particle size upon being subjected to toothbrushing in the mouth. Such agglomerates may be agglomerated with or without binding agent which may be water-soluble or water-insoluble.

For most purposes, it is preferable that the soft dental abrasive have a particle size less than 20 microns to avoid any gritty feel.

The proportion of such additional abrasive in the dentifrice is usually in the range of about 10–50%, and is preferably such that when calcium pyrophosphate is omitted from the dentifrice, the RDA (radioactive dentin abrasion) is in the range of about 100 to 600, preferably about 100 or 200 to 450. The RDA of a dentifrice when calcium pyrophosphate is the only abrasive is typically about 300 to 450. Typically, the proportion of additional abrasive is in the range of about 5 to 70% of the dentifrice, such as about 10 to 50%.

To make toothpastes or dental creams, calcium pyrophosphate and any other dental abrasives are dispersed in a dental vehicle which preferably contains a liquid which is water and/or a humectant such as glycerine, sorbitol, propylene glycol or polyethylene glycol 400, including suitable mixtures thereof. It is usually advantageous to use a mixture of both water and one or two humectants. Polyethylene glycols of suitable molecular weight, e.g., polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol. Typically, the vehicle contains about 0–80% of water.

The zinc compound may be added directly to the dental vehicle containing the abrasives, or the abrasives may be pretreated with an aqueous solution of the zinc compound particularly zinc chloride, and the pretreated abrasives added to a suitable dental vehicle. The zinc oxide is preferably added directly to the vehicle along with the abrasives because of its water-insolubility. The zinc chloride, being water-soluble, is preferably dissolved in an aqueous solution and stirred with the abrasive (typically all abrasives, if more than calcium pyrophosphate is used in the dentifrice). The solids are then isolated and washed with water. The zinc-treated abrasive is then incorporated into a dental vehicle. The unique reduction in enamel abrasiveness is the result of the combination of zinc compound and abrasive. When the abrasive is pretreated with zinc chloride substantially similar large reductions in enamel abrasivity of the finished dentifrices are observed with varying concentrations of zinc in the dentifrices. When the abrasives and zinc compound, particularly zinc oxide, are separately incorporated into the dentifrices, reductions in enamel abrasivity are increased with greater concentrations of zinc in the dentifrices.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, water-soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica e.g., synthetic finely divided silicas including those sold under the trademarks Cab-O-Sil M5, Syloid 244, Syloid 266 and Aerosil D200. The solid portion of the vehicle is typically present in an amount up to about 10% by weight of the toothpaste and preferably within about 0.5–8% by weight.

Fine particles of thermoplastic resin may also be present, such as particles of solid polymer having a molecular weight above 1000 (and preferably above 10,000, e.g., about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerizing or by grinding the polymer in bulk, and may be present in amount of up to about 60% or more of the dentifrice, e.g., in the range of about 20 to 60%, such as about 20 to 50%, e.g., about 30 to 50% in a toothpaste. Examples of thermoplastic resins are polymerized ethylenically unsaturated compounds, such as polyolefins (e.g., polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as Nylon (e.g., Nylon 6); cellulosics such as cellulose acetate, etc.

The toothpaste may also contain surface-active agent, e.g., to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents are water soluble salts of higher fatty acid monoglyceride monosulfates, such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine, and the sodium, potassium, and ethanolamine salts of N-lauroyl, N-myristyl or N-aplmityl sarcosinates, which should be substantially free from soap or similar higher fatty acid material which tends to be substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface active materials include nonionic agents such as condensates of sorbitan monostearate with approximately 60 moles of ethylene oxide, condensates of ethylene oxide with propylene oxide condensates of propylene glycol ("Pluronics") and cationic surface active germicides and antibacterial compounds such as di-isobutylphenoxyethyldimethyl benzyl ammonium chloride, benzyl dimethyl stearyl ammonium chloride, tertiary amines having one fatty acid group (of from 12 to 18 carbon atoms) and two (poly) oxyethylene groups attached to the nitrogen (typically containing a total of from about 2 to 50 ethenoxy groups per molecule) and salts thereof with acids, and compounds of the structure;

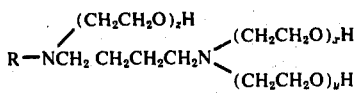

where R is a fatty alkyl group containing from about 12 to 18 carbon atoms, and $x$, $y$ and $z$ total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents such as titanium dioxide, preservatives, silicones, chlorophyl compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl)biguanide;
p-chlorophenyl biguanide;
4-chlorobenzhydryl biguanide;
4-chlorobenzhydrylguanylurea;
$N^1$-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1, 3-bis (2-ethylhexyl)-5-methylhexahydropyrimidine;

and their non-toxic acid addition salts.

Suitable flavoring or sweetening sialagogues may be employed in formulating a flavor for the composition of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate and saccharin. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride ($SnF_2$.KF), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water-soluble fluorine content thereof.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g., in vacuo) and tubed.

Preferably the amount of water-insoluble essential flavoring oil is above 0.5% and below 2%. Strongly flavored toothpastes contain above 1% of such flavoring oil, e.g., about 1.2 to 1.5%.

The following example is given to illustrate this invention further. In this application all proportions are by weight unless otherwise indicated.

EXAMPLE

A toothpaste of the following formulation is prepared and by analysis is observed to have an REA of 278 and an RDA of 398:

| Ingredients | Parts |
|---|---|
| Glycerine | 9.8 |
| Sorbitol | 11.9 |
| Sodium Carboxymethyl Cellulose | 1.4 |
| Sodium Silicate | 0.3 |
| Water | 30.5 |
| Calcium Pyrophosphate | 40.1 |
| Sodium Lauryl Sulfate | 0.8 |
| Sodium Coco-monoglyceride Sulfonate | 1.3 |
| Stannous Fluoride | 0.4 |
| Stannous Pyrophosphate | 1.0 |

When 0.4 parts of zinc oxide are incorporated therein the REA is 115 and the RDA is 358.

Additional samples of calcium pyrophosphate dentifrices of the above formulation have calculated REA values of 455, 244, and 313. The additions of zinc oxide and zinc chloride also effect substantial reductions in REA of these dentifrices.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dentifrice having superior cleaning and polishing characteristics containing an abrasive system including calcium pyrophosphate, which calcium pyrophosphate has been pre-treated with a non-toxic zinc compound in an amount to provide at least about 0.0065% by weight of zinc to the dentifrice, the amount of said zinc compound being up to about 1% by weight, to reduce the enamel abrasivity.

2. The dentifrice claimed in claim 1 wherein said calcium pyrophosphate is present in amount of at least about 7.5% by weight of the total.

3. The dentifrice claimed in claim 1 wherein the zinc compound is selected from the group consisting of zinc oxide and zinc chloride in an amount of about 0.01–1.0% by weight of the total.

4. The dentifrice claimed in claim 3 wherein said zinc compound is zinc oxide.

5. The dentifrice claimed in claim 4 wherein said zinc compound is zinc chloride.

6. The dentifrice claimed in claim 1 wherein said calcium pyrophosphate is present in amount of about 20–75% by weight of the total.

7. The dentifrice claimed in claim 6 wherein said calcium pyrophosphate is present in amount of about 40–50% by weight of the total.

* * * * *